(12) United States Patent
Harandi et al.

(10) Patent No.: US 11,890,446 B2
(45) Date of Patent: Feb. 6, 2024

(54) CAP FOR MALE AND FEMALE THREADED FITTINGS

(71) Applicant: Becton, Dickinson and Company, Franklin Lakes, NJ (US)

(72) Inventors: Amir Harandi, Bloomingdale, NJ (US); Chang Jiang, Butler, NJ (US); Paul P. Marici, Piscataway, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 229 days.

(21) Appl. No.: 17/229,144

(22) Filed: Apr. 13, 2021

(65) Prior Publication Data

US 2021/0322750 A1    Oct. 21, 2021

Related U.S. Application Data

(60) Provisional application No. 63/011,365, filed on Apr. 17, 2020.

(51) Int. Cl.
*A61M 39/16*     (2006.01)
*A61M 39/20*     (2006.01)
*A61M 39/10*     (2006.01)

(52) U.S. Cl.
CPC .......... *A61M 39/162* (2013.01); *A61M 39/20* (2013.01); *A61M 2039/1083* (2013.01); *A61M 2039/1088* (2013.01)

(58) Field of Classification Search
CPC ............................ A61M 39/162; A61M 39/20
See application file for complete search history.

(56) References Cited

U.S. PATENT DOCUMENTS

| | | | |
|---|---|---|---|
| 3,403,679 | A | 10/1968 | Sinclair et al. |
| 4,597,758 | A | 7/1986 | Aalto et al. |
| 4,642,102 | A | 2/1987 | Ohmori |
| 4,711,363 | A | 12/1987 | Marino |
| 4,738,376 | A | 4/1988 | Markus |

(Continued)

FOREIGN PATENT DOCUMENTS

| | | |
|---|---|---|
| CA | 2523133 C | 2/2013 |
| CN | 1322119 A | 11/2001 |

(Continued)

OTHER PUBLICATIONS

"Non-Final Office Action in U.S. Appl. No. 17/076,102 dated Aug. 24, 2021, 10 pages".

(Continued)

*Primary Examiner* — Bradley J Osinski
(74) *Attorney, Agent, or Firm* — Servilla Whitney LLC

(57) ABSTRACT

A cap for disinfecting a needleless connector is described herein. The cap includes a housing having a cavity and an insert disposed within. The insert includes one or more cantilevered prongs disposed on a distal wall of the insert. The one or more cantilevered prongs are configured to bend upon insertion of the needleless connector. On an outer sidewall of the one or more cantilevered prongs are one or more ledges extending at essentially a right angle to the one or more cantilevered prongs, the one or more ledges being configured to push against the sidewall of the housing to resist further bending of the one or more cantilevered prongs upon advancement of the needleless connector.

18 Claims, 8 Drawing Sheets

(56) References Cited

U.S. PATENT DOCUMENTS

| | | | |
|---|---|---|---|
| 4,906,231 A | 3/1990 | Young | |
| 5,084,017 A | 1/1992 | Maffetone | |
| 5,496,288 A | 3/1996 | Sweeney | |
| 5,676,406 A | 10/1997 | Simmons et al. | |
| 5,755,696 A | 5/1998 | Caizza | |
| 5,984,123 A | 11/1999 | Mogami et al. | |
| 6,565,529 B1 | 5/2003 | Kimber et al. | |
| 6,632,199 B1 | 10/2003 | Tucker et al. | |
| 7,083,605 B2 | 8/2006 | Miyahara | |
| 8,012,131 B2 | 9/2011 | Moser et al. | |
| 8,388,894 B2 | 3/2013 | Colantonio | |
| 8,647,308 B2 | 2/2014 | Solomon et al. | |
| 8,721,627 B2 | 5/2014 | Alpert | |
| 8,777,504 B2 | 7/2014 | Shaw et al. | |
| 8,961,475 B2 | 2/2015 | Solomon et al. | |
| 9,039,989 B2 | 3/2015 | Lui et al. | |
| 9,132,223 B1 | 9/2015 | Wakeel | |
| 9,192,449 B2 | 11/2015 | Kerr et al. | |
| 10,099,048 B2 | 10/2018 | Chiu et al. | |
| 10,166,381 B2 | 1/2019 | Gardner et al. | |
| 10,376,686 B2 | 8/2019 | Burkholz et al. | |
| 10,589,080 B2 | 3/2020 | Hitchcock et al. | |
| 10,603,481 B2 | 3/2020 | Avula et al. | |
| 10,871,246 B2 | 12/2020 | Marici et al. | |
| 11,353,147 B2 | 6/2022 | Marici | |
| 11,511,100 B2 | 11/2022 | Ryan | |
| 2003/0093009 A1 | 5/2003 | Newby et al. | |
| 2003/0209681 A1 | 11/2003 | Leinsing et al. | |
| 2004/0039341 A1 | 2/2004 | Ranalletta | |
| 2004/0044318 A1 | 3/2004 | Fiser et al. | |
| 2005/0147525 A1 | 7/2005 | Bousquet | |
| 2005/0197646 A1 | 9/2005 | Connell et al. | |
| 2007/0060904 A1 | 3/2007 | Vedrine et al. | |
| 2008/0010766 A1 | 1/2008 | Kaufman et al. | |
| 2008/0171995 A1 | 7/2008 | Vitullo et al. | |
| 2008/0177250 A1 | 7/2008 | Howlett et al. | |
| 2010/0000040 A1 | 1/2010 | Shaw et al. | |
| 2010/0049170 A1* | 2/2010 | Solomon | A61M 39/165 604/539 |
| 2010/0050351 A1* | 3/2010 | Colantonio | A61L 2/18 15/104.93 |
| 2010/0100056 A1 | 4/2010 | Cawthon et al. | |
| 2011/0046603 A1 | 2/2011 | Felsovalyi et al. | |
| 2011/0054440 A1 | 3/2011 | Lewis | |
| 2011/0213341 A1 | 9/2011 | Solomon et al. | |
| 2011/0264037 A1 | 10/2011 | Foshee et al. | |
| 2012/0039764 A1 | 2/2012 | Solomon et al. | |
| 2012/0111368 A1 | 5/2012 | Rahimy et al. | |
| 2012/0123386 A1 | 5/2012 | Tsals | |
| 2012/0302997 A1 | 11/2012 | Gardner et al. | |
| 2013/0085474 A1 | 4/2013 | Charles et al. | |
| 2013/0171030 A1 | 7/2013 | Ferlic et al. | |
| 2013/0197485 A1 | 8/2013 | Gardner et al. | |
| 2013/0338644 A1 | 12/2013 | Solomon et al. | |
| 2014/0052074 A1 | 2/2014 | Tekeste | |
| 2014/0150832 A1 | 6/2014 | Rogers et al. | |
| 2015/0094666 A1 | 4/2015 | Bates et al. | |
| 2016/0045629 A1 | 2/2016 | Gardner et al. | |
| 2016/0067422 A1 | 3/2016 | Davis et al. | |
| 2016/0158520 A1 | 6/2016 | Ma et al. | |
| 2017/0203087 A1 | 7/2017 | Ryan et al. | |
| 2018/0085568 A1 | 3/2018 | Drmanovic | |
| 2018/0200500 A1 | 7/2018 | Ziebol et al. | |
| 2018/0237190 A1 | 8/2018 | Iwasaki | |
| 2018/0243547 A1 | 8/2018 | Fox et al. | |
| 2018/0256879 A1* | 9/2018 | Chiu | A61M 39/20 |
| 2018/0256883 A1 | 9/2018 | Follman et al. | |
| 2019/0151643 A1 | 5/2019 | Alpert | |
| 2019/0234540 A1* | 8/2019 | Marici | A61M 39/165 |
| 2019/0308006 A1 | 10/2019 | Erekovcanski et al. | |
| 2019/0351212 A1 | 11/2019 | Dudar et al. | |
| 2020/0238070 A1 | 7/2020 | Ryan | |
| 2021/0100996 A1 | 4/2021 | Wijesuriya et al. | |
| 2021/0187267 A1 | 6/2021 | Jiang | |
| 2022/0273931 A1 | 9/2022 | Jiang et al. | |
| 2023/0080687 A1 | 3/2023 | Ryan | |

FOREIGN PATENT DOCUMENTS

| | | |
|---|---|---|
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103083767 A | 5/2013 |
| CN | 204161736 U | 2/2015 |
| CN | 206198472 U | 5/2017 |
| DE | 20017013 U1 | 12/2000 |
| DE | 10247963 A1 | 5/2004 |
| DE | 202005004079 U1 | 7/2006 |
| EP | 0589379 A1 | 3/1994 |
| EP | 2832391 A1 | 2/2015 |
| GB | 2408259 A | 5/2005 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008532701 A | 8/2008 |
| JP | 2008239164 A | 10/2008 |
| JP | 2010527276 A | 8/2010 |
| JP | 2012522593 A | 9/2012 |
| JP | 2015517377 A | 6/2015 |
| JP | 2016511119 A | 4/2016 |
| JP | 2016104214 A | 6/2016 |
| WO | 200024442 A1 | 5/2000 |
| WO | 2011066586 A1 | 6/2011 |
| WO | 2013046857 A1 | 4/2013 |
| WO | 2014159346 A1 | 10/2014 |
| WO | 2015127285 A1 | 8/2015 |
| WO | 2015174953 A1 | 11/2015 |
| WO | 2016158144 A1 | 10/2016 |
| WO | 2017087400 A1 | 5/2017 |
| WO | 2017095373 A1 | 6/2017 |
| WO | 2018106508 A1 | 6/2018 |
| WO | 2018237090 A1 | 12/2018 |
| WO | 2019212637 A1 | 11/2019 |
| WO | 2020112767 A1 | 6/2020 |

OTHER PUBLICATIONS

"PCT International Search Report and Written Opinion in PCT/US2021/027219 dated Oct. 22, 2021, 22 pages".
PCT International Search Report and Written Opinion in PCT/US2021/027214 dated Jul. 19, 2021, 14 pages.
PCT International Search Report and Written Opinion in PCT/US2021/027218 dated Jul. 22, 2021, 14 pages.
PCT International Search Report and Written Opinion in PCT/US2021/027220 dated Jul. 21, 2021, 15 pages.
PCT Invitation to Pay Additional Fees in PCT/US2021/027219, dated Jul. 22, 2021, 15 pages.
PCT Invitation to Pay Additional Fees in PCT/US2021/019546, dated Jun. 15, 2021, 17 pages.

* cited by examiner

CAP FOR MALE AND FEMALE THREADED FITTINGS

CROSS-REFERENCE TO RELATED APPLICATIONS

This application claims priority to U.S. Provisional Application No. 63/011,365, filed Apr. 17, 2020, the entire disclosure of which is hereby incorporated by reference herein.

TECHNICAL FIELD

The present disclosure generally relates to a device for disinfecting and sterilizing access ports with, e.g., male and female luer fitting, and, in particular, to disinfecting and sterilizing devices capable of accommodating multiple types of connectors. Generally, exemplary embodiments of the present disclosure relate to the fields of threaded fitting, including medical caps and medical disinfection caps, and in particular caps and/or disinfection caps for uses with fluid luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hubs and ports/valves upon connection to the VAD to deliver the fluid or pharmaceutical. Each access hub (or port/valve or connection) is associated with some risk of transmitting a catheter related bloodstream infection (CRBSI), which can be costly and potentially lethal.

In order to decrease CRBSI cases and to ensure VAD's are used and maintained correctly, standards of practice have been developed, which include disinfecting and cleaning procedures.

Disinfection caps have been added to the Society for Healthcare Epidemiology of America (SHEA) guidelines and the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

Throughout the sequence of procedures associated with the transmission of a microorganism that can cause a CRBSI, there are many risks of contact or contamination. Contamination can occur during drug mixing, attachment of a cannula, and insertion into the access hub. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Currently, caps for male needleless connectors, female needleless connectors, intravenous (IV), and hemodialysis lines use different designs and are, therefore, limited to the types of connectors to which the cap can be attached. Currently, there are male disinfecting cap devices for disinfecting ISO594-2 type of female threaded fluid luer connectors and there are female disinfecting cap devices for disinfecting ISO594-2 type of male threaded fluid luer connectors. However there is not a singular universal disinfecting cap device with features allowing it to interface with both a male and female type of threaded connectors. Thus, prior disinfecting caps were designed to fit one type of connector only, and were specific to one particular size and/or shape of connector. Thus, there is a need for a disinfecting device capable of accommodating multiple types of connectors, including both male and female connectors, to streamline the disinfecting process.

A need also exists to provide a disinfecting cap having a proper mechanical fit and alignment for mating to connectors and alerting the user when full engagement has been achieved, and thus a complete amount of disinfectant has been dispensed.

SUMMARY

A first aspect of the present disclosure relates to a cap comprising a substantially cylindrically shaped housing, a substantially cylindrically shaped insert and one or more cantilevered prongs. The substantially cylindrically shaped housing has a distal wall, an open proximal end and a sidewall, the sidewall having an inner surface and an outer surface, the inner surface, distal wall and open proximal end defining a cavity of the housing. The substantially cylindrically shaped insert has an open proximal end a closed distal end, the closed distal end defining a distal wall having an inner surface and an outer surface, the insert being removably disposed within the cavity of the housing, the outer surface of the distal wall of the insert abutting the distal wall of the housing. The one or more cantilevered prongs protrude from the inner surface of the distal wall of the insert, the one or more cantilevered prongs having a sidewall, the one or more cantilevered prongs being configured to bend to facilitate interference fit between the insert and the mating feature of a needleless connector. A cavity of the insert is defined by the inner surface of the insert, the sidewall of the one or more cantilevered prongs and the open proximal end of the insert. One or more ledges extend perpendicularly at essentially a right angle to the one or more cantilevered prongs, the one or more ledges being configured to push against the sidewall of the housing to resist further bending of the one or more cantilevered prongs upon advancement of the needleless connector. The cap further comprises an absorbent material.

In one or more embodiments, the syringe further comprises a centering feature of the housing disposed within the cavity of the housing. The centering feature protrudes from the distal wall of the housing, the centering feature of the housing being configured to intertidigate with a corresponding centering feature of the insert upon insertion of the insert into the cavity of the housing.

In one or more embodiments, the centering feature of the insert extends the outer surface of the insert partially into the distal wall of the insert, the centering feature being a ring-shaped channel.

In one or more embodiments, the one or more cantilevered prongs are separated by gaps. In one or more embodiments, the one or more cantilevered prongs are of a unitary cylindrical body.

In one or more embodiments, the one or more ledges are disposed at least partially the length of the one or more cantilevered prongs.

In one or more embodiments, the one or more ledges include a support rib positioned under the one or more ledges and affixed on the one or more cantilevered prongs, the support rib being configured to provide rigidity to the one or more ledges.

In one or more embodiments, the disinfectant is absorbed within the absorbent material. In one or more embodiments, the absorbent material is disposed within the cavity of the housing, the absorbent material being disposed between the distal wall of the housing and the outer surface of the distal wall of the insert.

In one or more embodiments, the absorbent material is disposed within the cavity of the insert.

In one or more embodiments, advancement of a needleless connector into the cavity of the insert causes compression of the absorbent material, whereby disinfectant is released.

In one or more embodiments, the diameter of the cavity of the housing is larger than the diameter of the insert.

In one or more embodiments, disinfectant escapes between the inner surface of the sidewall of the housing and the insert.

In one or more embodiments, the distal wall of the insert has a diameter R2 and the one or more cantilevered prongs have a diameter R1, the diameter R2 of the distal wall is greater than the diameter R1 of the one or more cantilevered prongs.

In one or more embodiments, a collar of a needleless connector is inserted in a gap formed between the one or more cantilevered prongs and the sidewall of the housing.

In one or more embodiments, the insert is configured to engage a female connector with respect to its inner sidewall, and engage a male connector with respect to its outer sidewall.

In one or more embodiments, an inner sidewall of the one or more cantilevered prongs includes at least one inner thread configured to mate with a thread of a needleless connector.

In one or more embodiments, the at least one inner thread is configured to mate with a male needleless connector. In one or more embodiments, the at least one outer thread is configured to mate with a female needleless connector.

DETAILED DESCRIPTION

Figures 1, 2A:
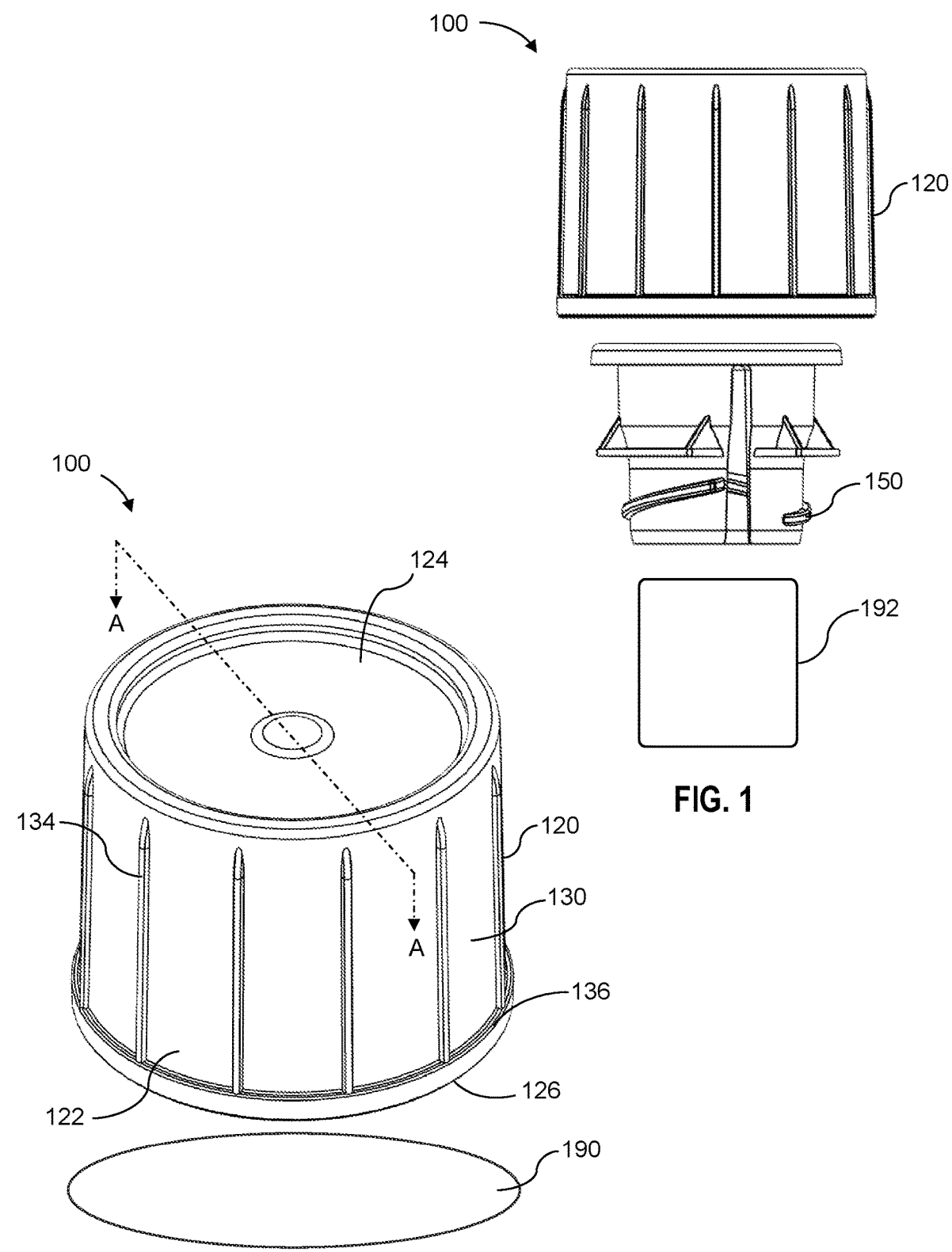
FIG. 1 illustrates an exploded view of a cap according to exemplary embodiments of the disclosure.
FIG. 2A illustrates an exploded view of the cap of FIG. 1.

Embodiments of the disclosure pertain to a sterile, universal cap for connection to and disinfection of a medical connector or a needleless connector, including male connectors and female connectors. The male connectors and female connectors can be male luer connectors and female luer connectors. The cap may further comprise absorbent material, a disinfectant or the antimicrobial agent and a peelable seal and/or septum. The cap provides a mechanical barrier for connectors and contains an antimicrobial agent for disinfection. The cap of the present disclosure allows the practitioner to streamline the disinfecting process.

With respect to terms used in this disclosure, the following definitions are provided.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a flush syringe and can interlock and connect to the female end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe.

As would be readily appreciated by skilled artisans in the relevant art, while descriptive terms such as "lock", "tip", "hub", "thread", "sponge", "prong", "protrusion", "tab", "wall", "top", "side", "bottom" and others are used throughout this specification to facilitate understanding, it is not intended to limit any components that can be used in combinations or individually to implement various aspects of the embodiments of the present disclosure.

The embodiments exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Exemplary embodiments of the present disclosure provide caps that can reduce the number of device types and logistics currently needed in the hospital setting for connecting, capping, and/or disinfecting male and female threaded fluid luer connectors, by roughly half by including in a single cap or device features allowing it to be used with both male and female threaded fittings.

In an exemplary implementation of the embodiments of present disclosure, a cap, connector cap or disinfecting cap includes integrated thread, or threads, and other features in any and all combinations allowing it to interface with both male and female threaded fittings.

According to further exemplary implementations of the embodiments of the present disclosure, configuration of structural elements making up the cap include one or more cantilevered prongs disposed in cap's inner cavity, the cantilevered prongs comprising an inner thread to connect to threads of a female medical connectors and an outer thread to connect to threads of a male medical connectors, to facilitate securing of the cap onto a female fitting or onto a male fitting, respectively.

According to yet further exemplary implementations of the embodiments of the present disclosure, both of the male and female threads coincide with each other on the inner and outer face of the threaded protrusion.

According to still further exemplary implementations of the embodiments of the present disclosure, the cantilevered prong may be in the form of a protrusion and may be of a split thread type in which the protrusion may bend or deflect in order to allow better interference fit compliance with the fittings.

According to still further exemplary implementations of the embodiments of the present disclosure, one or more ledges may be disposed on the cantilevered prong to restrict the angle of the deflection of cantilevered prongs, increasing the security of engagement when the disinfecting cap is connected to male or female connectors.

According to still further exemplary implementations of the embodiments of the present disclosure, the female threads are sized and have a thread pattern that will engage with a standard ISO594-2 type of male fitting and/or the male threads are sized and have a thread pattern that will engage with a standard ISO594-2 type of female fitting. An example of an ISO594-2 type of fitting is a Q-style fitting.

In one or more embodiments, the female connector may be selected from the group consisting essentially of needle-free connectors, catheter luer connectors, stopcocks, and hemodialysis connectors. In one or more embodiments, the needleless connector is selected from a Q-Syte connector, MaxPlus, MaxPlus Clear, MaxZero, UltraSite, Caresite, InVision-Plus, Safeline, OneLink, V-Link, ClearLink, NeutraClear, Clave, MicroClave, MicroClave Clear, Neutron, NanoClave, Kendall, Nexus, InVision, Vadsite, Bionector, etc.

In one or more embodiments, the male connector may be an intravenous tubing end, a stopcock or male lock luer.

Before describing several exemplary embodiments of the disclosure, it is to be understood that the disclosure is not limited to the details of construction or process steps set forth in the following description. The disclosure is capable of other embodiments and of being practiced or being carried out in various ways.

Referring now to the drawings, wherein like reference numerals designate identical or corresponding parts throughout the several views, embodiments of the present disclosure are described as follows.

FIG. 1 illustrates an exploded view of a disinfecting cap 100. The disinfecting cap 100 comprises an insert 150 removably disposed within an outer housing 120. In one or more embodiments, an absorbent material 192 is disposed within the insert 150. The absorbent material 192 containing a disinfectant fluid or gel.

Figure 2B:
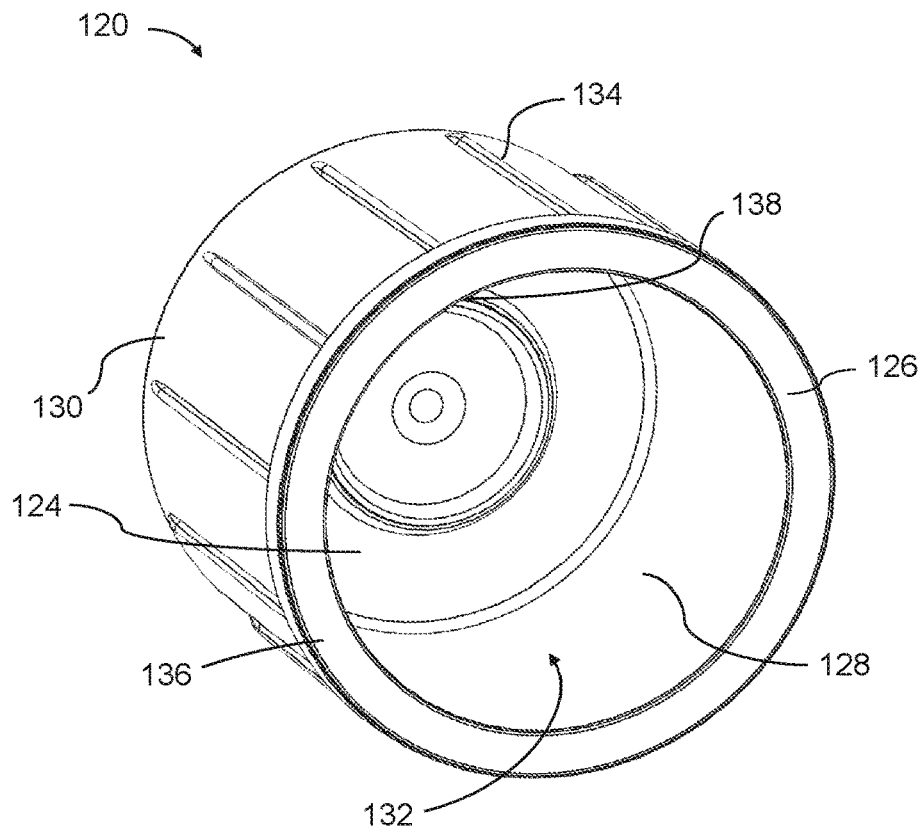
FIG. 2B illustrates a bottom perspective view of a housing of the cap of FIG. 1.
Figure 2C:
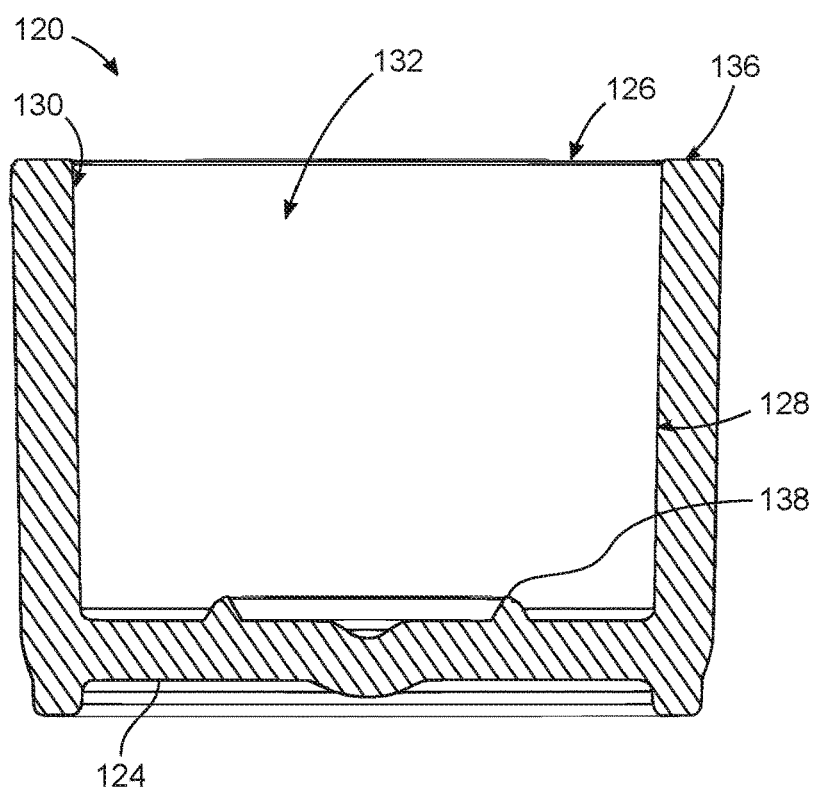
FIG. 2C illustrates a side cross-sectional view of the housing of FIG. 2B.

As shown in FIGS. 2A through 2C, the housing 120 is of a substantially cylindrical shape comprising an essentially cylindrical sidewall 122, a distal wall 124 and an open proximal end 126. The sidewall 122 includes an inner surface 128 and an outer surface 130. A cavity 132 is defined by the distal wall 124, the open proximal end 126 and the inner surface 128. In one or more embodiments, the outer surface 130 of sidewall 122 comprises a plurality of grip members 134. The open proximal end 126 of the housing 120 includes an engagement surface 136 on which a removable peelable seal 190 is disposed on.

In one or more embodiments, the peelable seal 190 is disposed on the engagement surface 136 of the open proximal end 126 of the housing 120 to prevent the disinfectant or the antimicrobial agent from exiting the cavity 132. With the absorbent material 192 fully inserted into the cavity 132 of the housing 120, the peelable seal 190 may be secured to the engagement surface of open proximal end 126 of housing 120. The peelable seal 190 minimizes entry of potential particulate hazard, provides a substantially impermeable enclosure for the cap 100, provides a leak prevention and protection enclosure, protects the contents of absorbent material 192 contained within the cavity 132, and/or maintains a sealed, sterilized environment. The peelable seal 190 provides a sufficient seal at a range of temperatures, pressures, and humidity levels.

In yet another exemplary implementation, a disinfecting member or members, such as an absorbent material 192, in the form of an isopropyl alcohol (IPA) soaked sponge and/or sponge is disposed within the cavity 132. In one or more embodiments, absorbent material 192 can also be formed together as a single cleaning member or separate cleaning member provided within cavity 132.

In one or more embodiments, as best shown in FIGS. 2B and 2C, a centering feature 138 is disposed within the cavity 132, the centering feature 138 extending from the distal wall 124. As shown, the centering feature 138 is in the form of a protruding ring being centered on the distal wall 124 of the housing 120. In one or more embodiments, the protruding ring of the centering feature 138 has chamfered walls. In one or more embodiments, the protruding ring of the centering feature 138 has rounded walls. The centering feature 138 of the housing 120 is configured to intertidigate with a corresponding centering feature (not shown) of the insert 150 upon advancement or insertion of the insert 150 into the cavity 132 of the housing 120, as discussed in further detail below.

Figure 3:
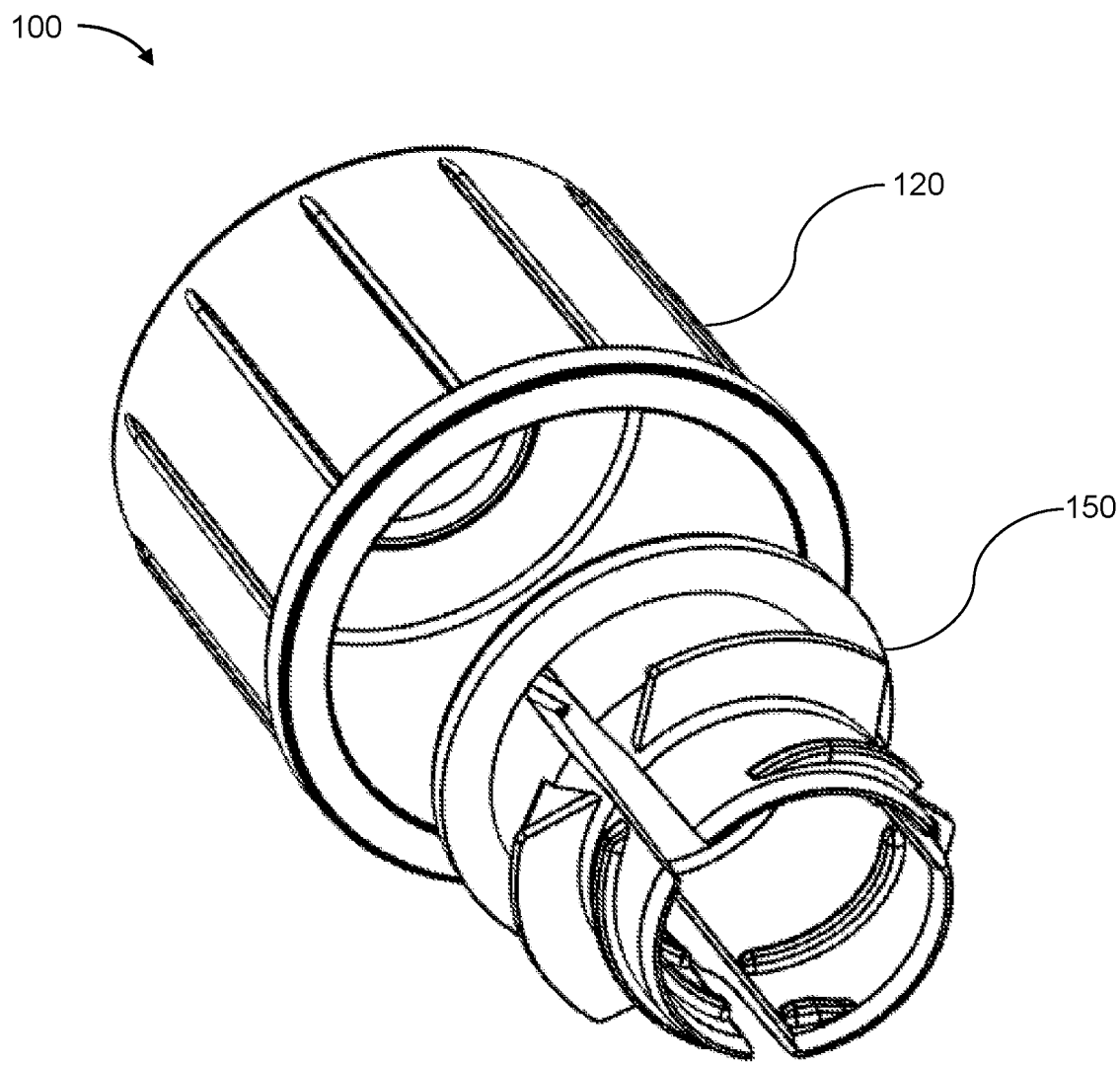
FIG. 3 illustrates an exploded view of the cap of FIG. 1.
Figure 4:
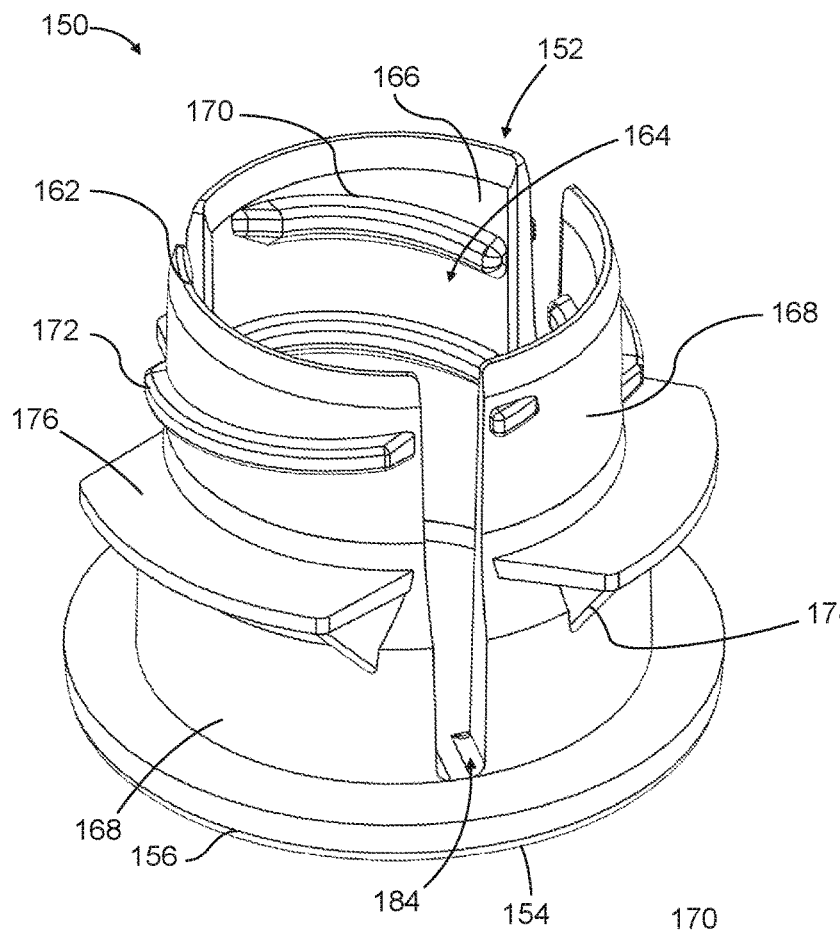
FIG. 4 illustrates a side perspective view of an insert of the cap of FIG. 1.
Figure 8:
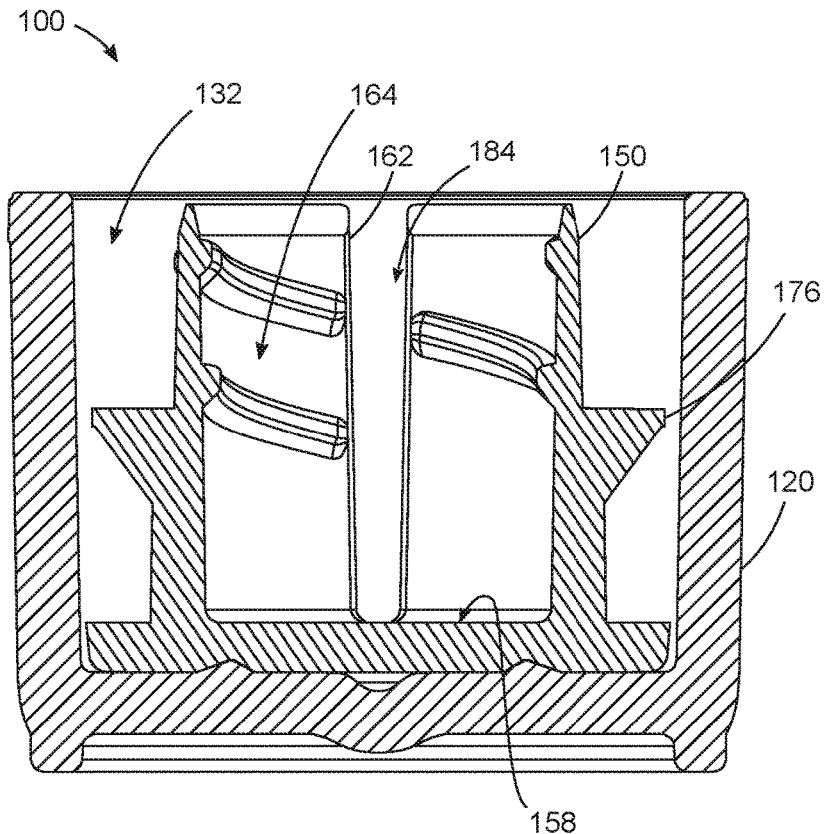
FIG. 8 illustrates a side cross-sectional view of the insert disposed within the housing of FIG. 1.

As shown in FIGS. 3 and 8, the insert 150 is advanceable or inserted into the cavity 132 of the housing 120 along a longitudinal direction. Upon full advancement, the insert 150 abuts the distal wall 124 of the housing 120. In one or more embodiments, the absorbent material 192 is disposed within the cavity 132 of the housing 120. In one or more embodiments, the advancement of the insert 150 causes longitudinal compression of the absorbent material 192, thereby dispensing disinfectant absorbed by the absorbent material 192. In one or more embodiments, the advancement of a needleless connector along a longitudinal direction to contact the insert 150 and subsequently cause longitudinal compression of the absorbent material 192, thereby dispensing disinfectant. In one or more embodiments, the diameter of the cavity 132 of the housing 120 is larger than the diameter of the insert 150, thereby allowing dispensed disinfectant to escape between the inner surface 128 of the sidewall 122 of the housing 120 and the insert 150.

As shown in FIGS. 4 through 7, the insert 150 has a substantially cylindrical body having an open proximal end 152 and a closed distal end 154 having a distal wall 156. The distal wall 156 has a substantially cylindrical shape having an inner surface 158 and an outer surface 160. From the inner surface 158 of the distal wall 156 protrudes one or more cantilevered prongs 162. The one or more cantilevered prongs 162 are separated by gaps 184 between each other. The one or more cantilevered prongs 162 have a generally cylindrical shape. The one or more cantilevered prongs 162 have a generally discontinuous cylindrical shape caused by the gaps 184 separating the one or more cantilevered prongs 162. In one or more embodiments, one or more cantilevered prongs can be configured to bend to facilitate interference fit between the insert 150 and the mating feature of the male needleless connector or female needleless connector. In one or more embodiments, the insert 150 can extend essentially from the inner surface 158 of the distal wall 156 toward the open proximal end 126 of the housing 120. In one or more embodiments, the one or more cantilevered prongs 162 extend essentially parallel to the sidewall 122 of the housing 120.

In an alternate embodiment, the one or more cantilevered prongs 162 are of a unitary cylindrical body, wherein no gaps 184 separate portions of the unitary cylindrical body. In one or more embodiments, the insert having a unitary body without any gaps 184 comprising any number of identical and/or different (in any dimensional characteristics, such as length width, thickness, or shape) prongs, as long as the insert is configured to engage a female connector with respect to its inner surface, and engage a male connector with respect to its outer surface.

In one or more embodiments, an inner sidewall 166 of the one or more cantilevered prongs 162 includes at least one inner thread 170 configured to mate with a thread of a female needleless connector. In one or more embodiments, an outer sidewall 168 of the one or more cantilevered prongs 162 includes at least one outer thread 172 configured to mate with a thread of a male needleless connector. In one or more embodiments, the at least one inner thread 170 and the at least one outer thread 172 are of a helical pattern.

Figure 5:
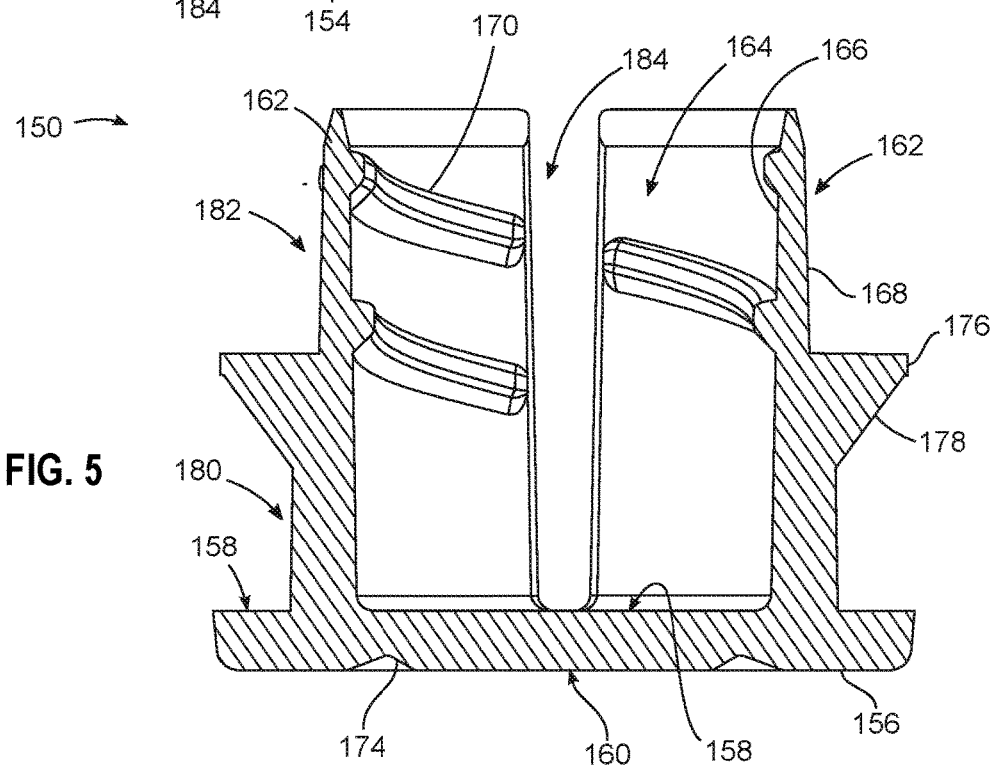
FIG. 5 illustrates a side cross-sectional view of the insert of FIG. 1.

As shown in FIG. 5, the at least one inner thread 170 can be included on the inner sidewall 166 of the one or more cantilevered prongs 162, the at least one inner thread 170 being sufficient to interlock with a mating feature of the needleless connector. In one or more embodiments, the least one inner thread 170 has a size and pitch to engage a threadable segment of a needleless connector, such as for example, a female luer connector. Such connectors are generally and commonly used as catheter and other fluid-tight protective connectors in medical applications. In one or more embodiments, cap 100 provides a protective cover for a female luer connector when engaged with the connector when threads from the female luer connector engage and form a releasable connection with the at least one inner thread 170.

In still yet further exemplary implementation, a profile of the at least one inner thread 170 and/or the inner sidewall 166 can essentially parallel, or coincide with, a profile of the at least one outer thread 172 and/or the outer sidewall 168, respectively.

Figure 6:
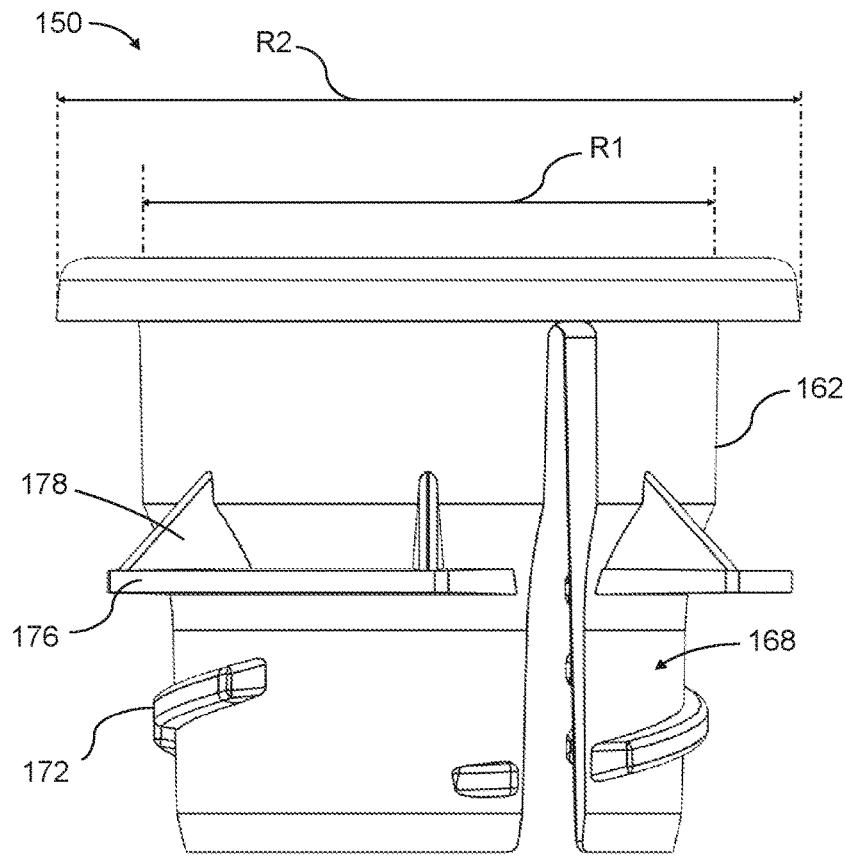
FIG. 6 illustrates a side view of the insert of FIG. 1.

As shown in FIGS. 5 and 6, in one or more embodiments, the one or more cantilevered prongs 162 have a distal portion 180 and a proximal portion 182, the distal portion 180 having a greater wall thickness than a wall thickness of the proximal portion 182. The wall thickness of each of the distal portion 180 and proximal portion 182 defined as the distance between the inner sidewall 166 and outer sidewall 168 of the one or more cantilevered prongs 162. In one or more embodiments, the outer sidewall tapers inwardly from the distal portion 180 to the proximal portion 182.

A cavity 164 of the insert 150 is defined by the distal wall 156, the inner sidewall 166 of the one or more cantilevered prongs 162 and the open proximal end 152. The cavity 164 is configured to receive a needleless connector, such as, by way of example, a female luer connector. In one or more embodiments, an inner sidewall 166 of the cantilevered prongs 162 includes at least one inner thread 170 configured to mate with a thread of a female needleless connector. In one or more embodiments, the at least one inner thread 170 extends from the open proximal end 152 at least partially the length of the one or more cantilevered prongs 162. In one or more embodiments, the at least one inner thread 170 extends from the open proximal end 152 to the distal wall 156.

As best shown in FIG. 6, the distal wall 156 has a diameter R2 and the distal portion 180 of the one or more cantilevered prongs 162 has a diameter R1. The diameter R2 of the distal wall 156 is greater than the diameter R1 of the distal portion 180 of the one or more cantilevered prongs 162 such that the one or more cantilevered prongs 162 extend from the inner surface 158 of the distal wall 156 and not from an edge of the distal wall 156. This configuration permits a collar of a needleless connector to be inserted in a gap 184 formed between the outer sidewall 168 of the one or more cantilevered prongs 162 and the inner surface 128 of the sidewall 122 of the housing 120, as shown in FIGS. 7A and 7B. In one or more embodiments, insert 150 is configured to engage a female connector with respect to its inner sidewall 166, and engage a male connector with respect to its outer sidewall 168. Likewise, the at least one inner thread 170 are configured to engage threads of a female needleless connector and the at least one outer thread 172 are configured to engage threads of a male needleless connector.

Referring to FIGS. 7 through 10, a centering feature 174 of the insert 150 is disposed on the outer surface 160 of the distal wall 156 of the insert 150, the centering feature 138 extending from the outer surface 160 partially into the distal wall 156. As shown, the centering feature 174 is in the form of a ring-shaped channel being centered on the distal wall 156 of the insert 150. In one or more embodiments, the channel of the centering feature 174 has chamfered walls. In one or more embodiments, the channel of the centering feature 174 has rounded walls. The centering feature 174 of the insert 150 is configured to intertidigate with the corresponding centering feature 138 of the housing 120 upon longitudinal advancement or insertion of the insert 150 into the cavity 132 of the housing 120, the centering feature of the housing 120 being disposed on the inner surface 128 if the distal wall 124 of the housing 120.

Figure 9:
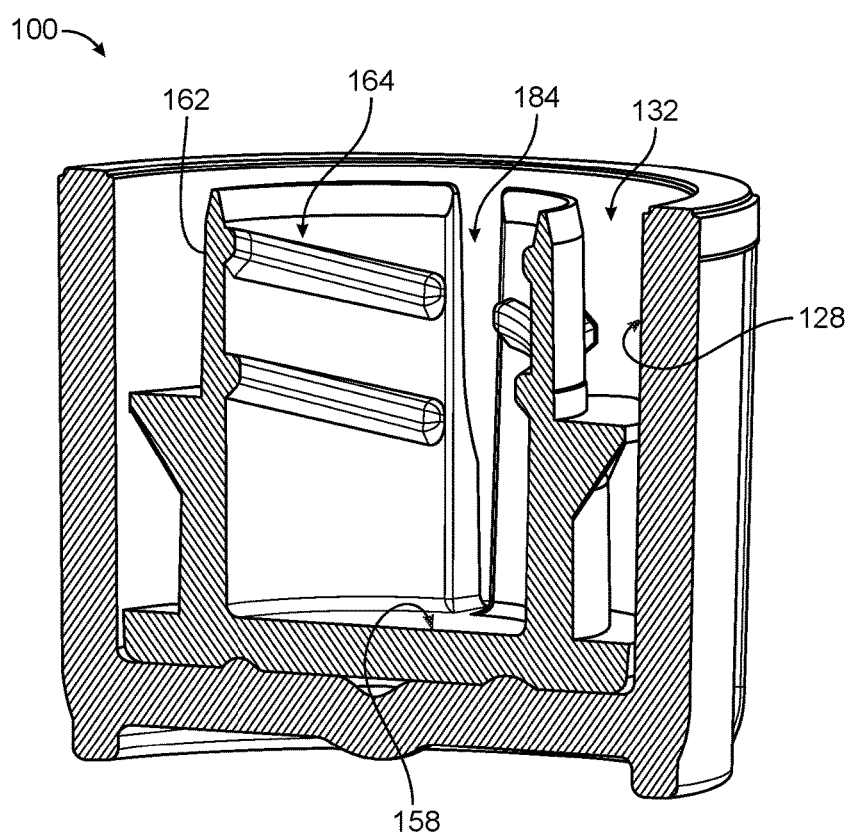
FIG. 9 illustrates a perspective cross-sectional view of the insert disposed within the housing of FIG. 1.
Figure 10:
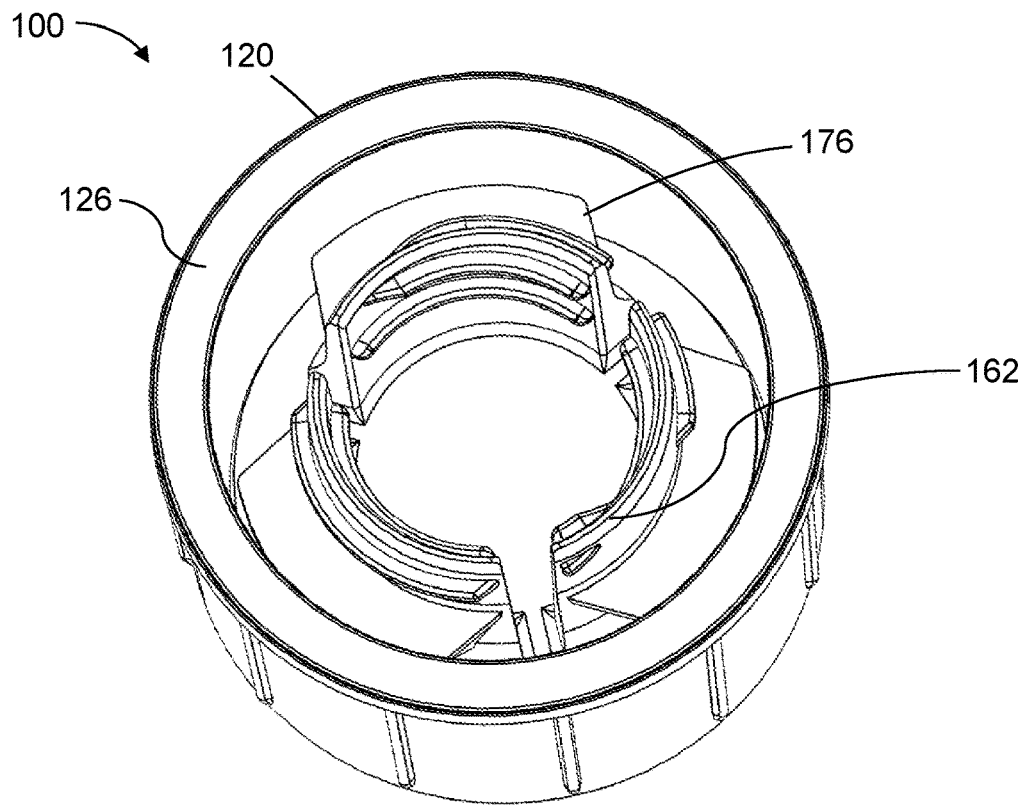
FIG. 10 illustrates a bottom perspective view of the insert disposed within the housing of FIG. 1.
Figure 11:
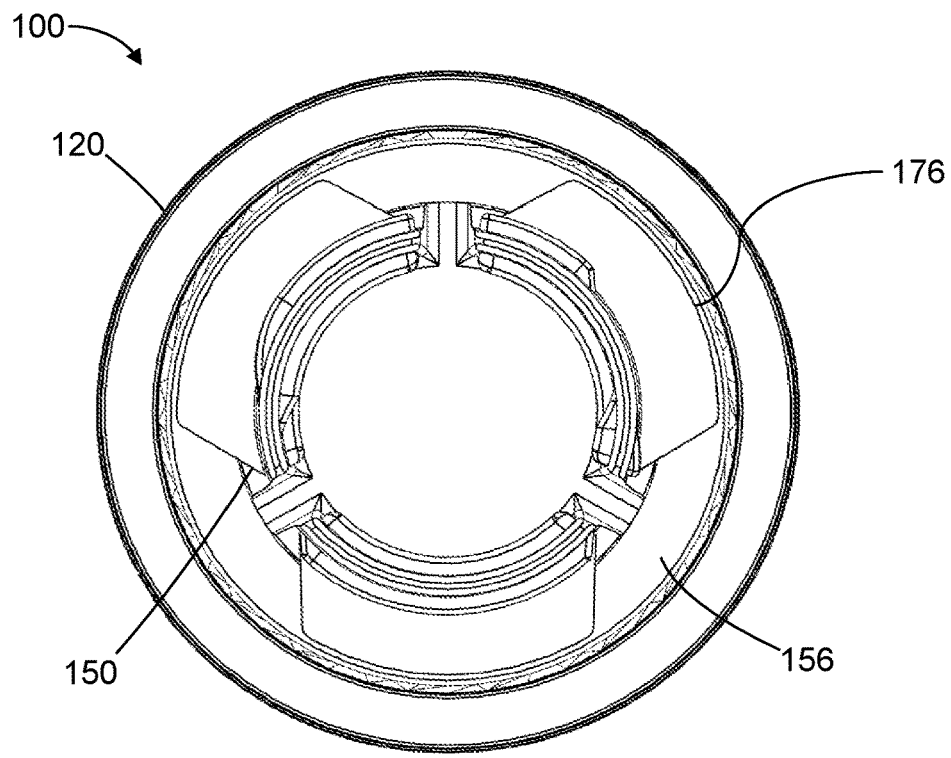
FIG. 11 illustrates a bottom view of the insert disposed within the housing of FIG. 1.

As shown in FIGS. 8 through 10, the insert 150 is fully disposed in the cavity 132 of the housing 120. The insert 150 has a length from the open proximal end 152 to the distal end 154, the length of the insert being less than the length of the cavity 132 of the housing 120 such that the insert 150 does not protrude beyond the cavity 132 of the housing 120. Compression of the absorbent material 192 in a longitudinal direction toward the distal wall 124 of housing 120 upon connection to the female luer connector or the male luer connector allows the connector to contact the disinfectant or antimicrobial agent to disinfect the female luer connector or the male luer connector.

Referring to FIGS. 3 through 11, the insert 150 further includes one or more ledges 176. The one or more ledges 176 extend perpendicularly at essentially a right angle to the one or more cantilevered prongs 162 of the insert 150. The one or more ledges 176 are disposed and protrude from at least partially a distance from the distal wall 156 along the one or more cantilevered prongs 162.

The one or more ledges 176 increases the mechanical fit of needleless connectors to the cap 100. As a needleless connector is mechanically secured to the insert 150, the one or more cantilevered prongs 162 are pushed radially outward. Consequently, the one or more ledges 176 are pushed against the sidewall 122 of the housing 120 to resist further radial motion or deflection of the one or more cantilevered prongs 162. The resistance from the one or more ledges 176 increases the torque requirement and separation force to disengage connectors from the cap, improving the securement of the cap 100 on the connectors. The resistance is noticeable by the user, thereby notifying the user that the needleless connector has been sufficiently advanced to a final position whereby the disinfectant is fully dispersed from the absorbent material 192 due to compression of the absorbent material 192. Additionally, the one or more ledges 176 equally displace radially outward towards the sidewall 122 of the housing 120 to improve the alignment of the cap 100 when secured to the medical connector. Furthermore, one or more ledges 176 can resist further engagement of a mechanical connection between two components. The one or more ledges 176 prevent further threaded connection between the cap 100 and a needleless connector. The one or more ledges 176 engaged with the medical connector will alert the user that full engagement between the threads of the threaded insert and needleless connector is secured. In one or more embodiments, the one or more ledges 176 engaged with the needleless connector and serve as a physical stop to prevent further advancement of the needleless connector into the cavity and thereby will alert the user that full engagement between the threads of the threaded insert and needleless connector is secured. The one or more ledges 176 restrict the angle of the deflection of the one or more cantilevered prongs 144, increasing the security of engagement when the cap 100 is connected to a needleless connector. The placement distance of the one or more ledges 176 on the one or more cantilevered prongs 162 can be configured to restrict the desired angle of deflection.

In one or more embodiments, the one or more ledges 176 are transverse to the one or more cantilevered prongs 162. The length of the one or more ledges 176 completely extend across the arcuate length of the one or more cantilevered prongs 162 of the insert 150

Figure 7:
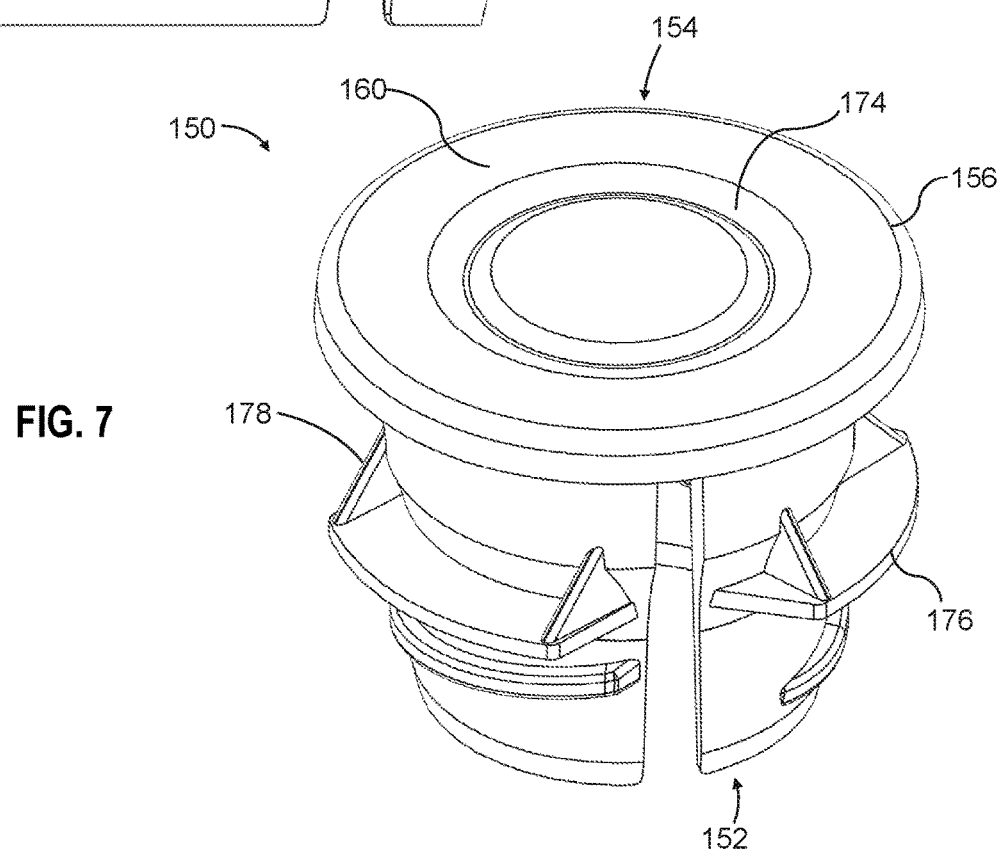
FIG. 7 illustrates a top perspective view of the insert of FIG. 1.

As shown in FIG. 7, in one or more embodiments, the one or more ledges 176 includes a support rib 178 positioned under the one or more ledges 176 and affixed on the one or more cantilevered prongs 162 of the insert 150. The support rib 178 is configured to provide rigidity to the one or more ledges 176. In one or more embodiments, the support rib 178 is integrated with the one or more ledges 176. In the preferred embodiment, the one or more ledges 176 are supported by one or more support ribs 178.

The one or more cantilevered prongs 162 and/or insert 150 may have varying shapes including, but not limited to, the shape of a trapezoid, an inverted trapezoid, a convex inner surface (for example a paraboloid), concave inner surface, or a straight profile (i.e., cylindrical or semi-conical shape). In one or more embodiments, the one or more cantilevered prongs tapers inward from the distal wall 156 of the insert toward the open proximal end. In one embodiment, insert 150 is integrally formed with the housing 120 and is positioned within the cavity 132 of the housing 120.

Figure 12A:
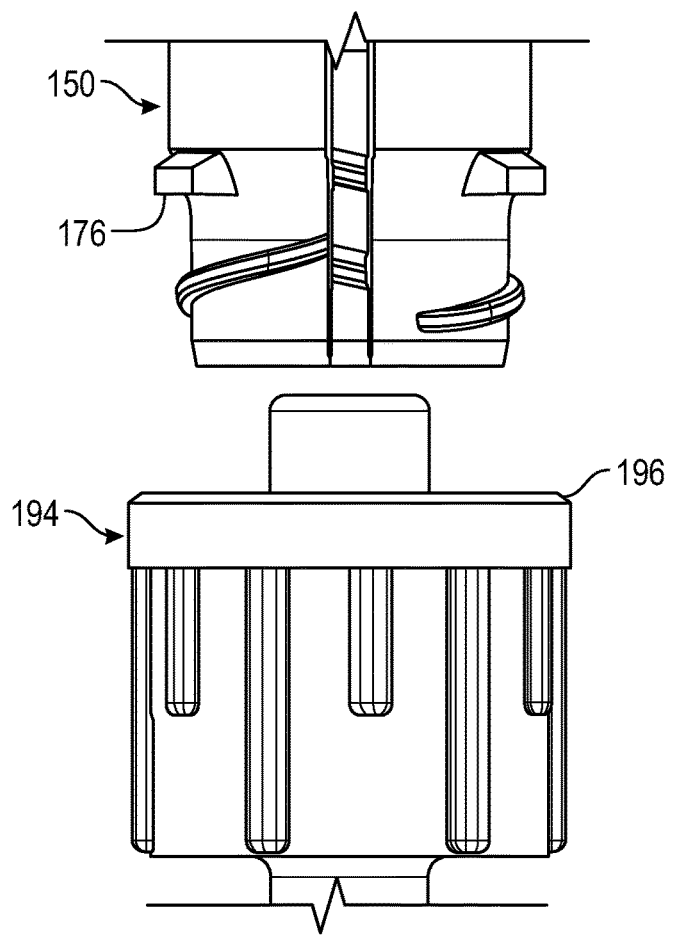
FIG. 12A illustrates an exploded view the insert of FIG. 1 and a needleless connector.
Figure 12B:
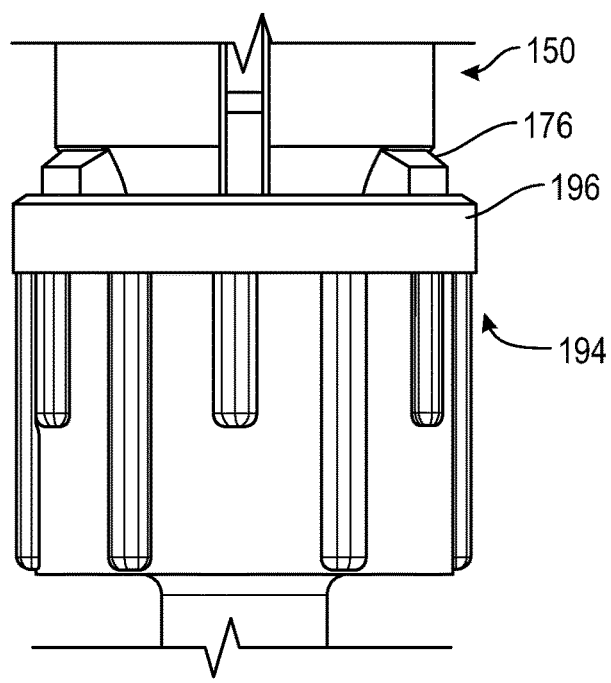
FIG. 12B illustrates the insert of FIG. 1 partially disposed within the needleless connector.

FIGS. 12A and 12B illustrate how the insert 150 engages with a needleless connector 194. For purposes of illustration, the housing 120 is not shown, however it should be understood that the needleless connector 194 is ultimately covered by the housing 120. The one or more ledges 176 disposed on the one or more cantilevered prongs 162 is configured to limit how deep a needleless connector 194 can be threaded or inserted into the insert. The needleless connector 194 is threadably fastened to the insert 150 and the one or more ledges 176 disposed on the one or more cantilevered prongs 162 control or limit the depth the needleless connector 194 can be threaded onto the insert 150 as the one or more ledges 176 mechanically abut the needleless connector 194 upon the desired insertion.

In one or more embodiments, the absorbent material 192 is under radial compression by the inner sidewall 166 of the insert 150 to retain the absorbent material 192 in the cavity 164 of the insert 150.

The cap 100 can achieve disinfection when used on needleless or luer connectors by integrating disinfectant or antimicrobial agent in the cavity 132 of the cap 100. The disinfectant or antimicrobial agent can be directly included in the cavity 132, or disinfectant or antimicrobial agent can be absorbed into sponges or foam material that fills the chamber of cap 100, such as the absorbent material 192. The cap 100 is configured to be compatible in interacting with various disinfectants.

Housing 120 and insert 150 are made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the housing 120 comprises a polypropylene or polyethylene material.

Referring to, in one or more embodiments, the peelable seal 190 is disposed on the engagement surface of open proximal end 126 of housing 120 to prevent the disinfectant or the antimicrobial agent from exiting the cavity 132. With the absorbent material 192 properly inserted into the cavity 132 of the cap 100, the peelable seal 190 may be secured to the engagement surface of open proximal end 126 of housing 120. The peelable seal 190 minimizes entry of potential particulate hazard and also provides a substantially impermeable enclosure for the cap 100, provides a leak prevention and protection enclosure, protects the contents of absorbent material contained within the cavity 132, and/or maintains a sealed, sterilized environment. The peelable seal 190 provides a sufficient seal at a range of temperatures, pressures, and humidity levels.

In one or more embodiments, the peelable seal 190 comprises an aluminum or multi-layer polymer film peel back top. In a specific embodiment, the peelable seal 190 is heat-sealed or induction sealed to the end face of the locking lid or to the cap open end. In one or more embodiments, the peelable seal 190 comprises a moisture barrier.

In one or more embodiments, the peelable seal 190 comprises an aluminum or multi-layer polymer film peel back top. In a specific embodiment, the peelable seal 190 is heat-sealed or induction sealed to the open end of the cap. In one or more embodiments, the peelable seal 190 comprises a moisture barrier. In one or more embodiments, the peelable seal 190 is thin enough to be punctured by the needleless connector such that the needleless connector can be inserted or advanced into the housing 120 without having to first remove the peelable seal 190.

In one or more embodiments, the absorbent material 192 is a nonwoven material, foam, or a sponge. In a specific embodiment, the foam is polyurethane foam. In a specific embodiment the absorbent material 192 is in the form of a foam plug. In one or more embodiments, the absorbent material 192 includes one or more slits.

In one or more embodiments, the insert 150 and the housing 120 can be bonded together through ultrasonic welding or solvent resistant biocompatible adhesive. In one or more embodiments, the insert 150 and housing 120 can also be interlocked through interference fit or snap fit.

The cap 100 can achieve disinfection when used on luer connectors by integrating disinfectant or antimicrobial agent in the cavity 132 of the housing 120 and/or the cavity 164 of the insert 150. The disinfectant or antimicrobial agent can be directly included in the cavity 132 of the housing 120 and/or the cavity 164 of the insert 150 or disinfectant or antimicrobial agent can be absorbed into sponges or foam material that fills the cavity 132 of the housing 120 and/or the cavity 164 of the insert 150. The cap 100 is configured to be compatible in interacting with various disinfectants. In one or more embodiments, the disinfectant or antimicrobial agent may include variations of alcohol or chlorhexidine. In one or more embodiments, the disinfectant or antimicrobial agent is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorhexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

According to exemplary embodiments of the disclosure as shown in FIGS. 12A and 12B, the housing 120 can receive a tip or hub of a needleless connector, for example after the peelable seal 190 is removed or pierced. By way of example, a female needleless or luer connector having a collar and a tip is received within the cavity 132 of the housing 120 and the cavity 164 of the insert 150, wherein the tip is advanced within the cavity 164 of the insert 150 and the collar is received within the cavity 132 of the housing 120. Where the insert 150 is disposed within the cavity 132 of the housing 120, the collar is disposed between the one or more cantilevered prongs 162 of the insert 150 and the sidewall 122 of the housing. By way of example, a male luer connector or stopcock is received within the cavity 132 of the housing. Where the insert 150 is disposed within the cavity 132, the male luer connector is disposed between the one or more cantilevered prongs 162 of the insert 150 and the sidewall 122 of the housing. The at least one inner thread 170 and/or the at least one outer thread 172 is configured to mate and secure the thread of a female or male luer connector. Such thread of a male or female luer connector may be, in one or more embodiments, one or more protrusions, lugs and/or a thread.

As shown in FIG. 12B, upon full advancement of the needleless connector 194 into the cap 100, the one or more ledges 176 abuts a collar 196 of the needleless connector 194, thereby preventing further advancement of the needleless connector 194 into the cap 100. The housing (not shown) of the cap 100 envelopes the collar 196 upon full advancement of the needleless connector 194. In operation, advancement of a needleless connector into the cavity 164 of the insert 150 causes compression of the absorbent material 192, whereby disinfectant is released due to compression of the absorbent material 192. In one or more embodiments, the absorbent material 192 is disposed within the cavity 132 of the housing, the absorbent material 192 being disposed between the distal wall 124 of the housing and the insert 150, whereby advancement of the needleless connector into the cavity 164 causes the insert 150 to compress the absorbent material 192 against the distal wall 124 of the housing 120. In one or more embodiments, the absorbent material 192 is disposed within the cavity 164 of the insert 150, whereby advancement of the needleless connector causes compression of the absorbent material 192 against the distal wall 156 of the insert 150.

While the present disclosure has been shown and described with reference to certain exemplary embodiments thereof, it will be understood by those skilled in the art that various changes in form and details may be made therein without departing from the spirit and scope of the embodiments of the present disclosure. For example, a disinfection sponge can comprise any suitable disinfecting or other application-specific substance, and can be made of any suitable material. Also, the inner and/or the outer housing of the cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to be limiting.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

The invention claimed is:

1. A cap comprising:
   a substantially cylindrically shaped housing having a distal wall, an open proximal end and a sidewall, the sidewall having an inner surface and an outer surface, the inner surface, the distal wall and the open proximal end defining a cavity of the housing;
   a substantially cylindrically shaped insert having a distal wall having an inner surface and an outer surface, the insert being removably disposed within the cavity of the housing, the outer surface of the distal wall of the insert abutting the distal wall of the housing;
   one or more cantilevered prongs protruding from the inner surface of the insert, the one or more cantilevered prongs having a sidewall defining a length, the one or more cantilevered prongs being configured to bend to facilitate interference fit between the insert and a mating feature of a needleless connector;
   a cavity of the insert defined by the inner surface of the insert, the sidewall of the one or more cantilevered prongs and the open proximal end of the insert
   a centering feature of the housing disposed within the cavity of the housing, the centering feature of the housing extends the outer surface of the housing partially into the distal wall of the insert, the centering feature being a ring-shaped channel, and
   an absorbent material.

2. The cap of claim 1, wherein the centering feature protrudes from the distal wall of the housing, the centering feature of the housing configured to interdigitate with a corresponding centering feature of the insert upon insertion of the insert into the cavity of the housing.

3. The cap of claim 1, wherein two or more cantilevered prongs are separated by gaps.

4. The cap of claim 1, wherein the one or more cantilevered prongs project from the insert.

5. The cap of claim 1, wherein a disinfectant is absorbed within the absorbent material.

6. The cap of claim 5, wherein the absorbent material is disposed within the cavity of the housing.

7. The cap of claim 6, wherein advancement of the insert into the cavity of the housing causes compression of the absorbent material, whereby disinfectant is released.

8. The cap of claim 1, wherein the absorbent material is disposed within the cavity of the insert.

9. The cap of claim 8, wherein advancement of a needleless connector into the cavity of the insert causes compression of the absorbent material, whereby disinfectant is released.

10. The cap of claim 1, wherein a diameter of the cavity of the housing is larger than the diameter of the insert.

11. The cap of claim 10, wherein the disinfectant is capable of escaping between the inner surface of the sidewall of the housing and the insert.

12. The cap of claim 1, wherein the distal wall of the insert has a diameter R2 and the one or more cantilevered prongs have a diameter R1, the diameter R2 of the distal wall is greater than the diameter R1 of the one or more cantilevered prongs.

13. The cap of claim 12, further comprising a gap formed between the one or more cantilevered prongs and the sidewall of the housing.

14. The cap of claim 1, wherein the insert is configured to engage a female connector with respect to its inner sidewall, and engage a male connector with respect to its outer sidewall.

15. The cap of claim 14, wherein an inner sidewall of the one or more cantilevered prongs includes at least one inner thread configured to mate with a thread of a needleless connector.

16. The cap of claim 1, further comprising one or more ledges extending perpendicularly at essentially a right angle to the one or more cantilevered prongs, the one or more ledges being configured to push against the sidewall of the housing to resist further bending of the one or more cantilevered prongs upon advancement of the needleless connector.

17. The cap of claim 16, wherein the one or more ledges are disposed at least partially the length of the one or more cantilevered prongs.

18. The cap of claim 16, wherein the one or more ledges include a support rib positioned under the one or more ledges and affixed on the one or more cantilevered prongs, the support rib being configured to provide rigidity to the one or more ledges.

* * * * *